US006919202B2

(12) United States Patent
Lewis et al.

(10) Patent No.: US 6,919,202 B2
(45) Date of Patent: Jul. 19, 2005

(54) UTILIZATION OF INVERTEBRATE LEARNING FOR FLEXIBLE AND SENSITIVE MONITORING AND IDENTIFICATION OF CHEMICALS

(75) Inventors: Wallace J. Lewis, Tifton, GA (US); James H. Tumlinson, Julian, PA (US); Dawn M. Olson, Tifton, GA (US); Glen C. Rains, Tifton, GA (US); Keiji Takasu, Fukuoka (JP); Torsten Meiners, Berlin (DE); Veronique Kerguelen, Overton (GB); Felix Waeckers, Rhenen (NL); Claire Bonifay, Ennetbaden (CH)

(73) Assignees: The United States of America, as represented by the Secretary of Agriculture, Washington, DC (US); University of Georgia Research Foundation, Inc., Athens, GA (US)

( * ) Notice: Subject to any disclaimer, the term of this patent is extended or adjusted under 35 U.S.C. 154(b) by 372 days.

(21) Appl. No.: 09/826,146

(22) Filed: Apr. 5, 2001

(65) Prior Publication Data

US 2003/0148529 A1 Aug. 7, 2003

Related U.S. Application Data

(60) Provisional application No. 60/195,218, filed on Apr. 7, 2000.

(51) Int. Cl.[7] ............................. C12M 1/34; C12Q 1/00
(52) U.S. Cl. ......................... 435/287.1; 435/4; 436/63; 422/98; 119/6.5; 119/421; 119/712; 449/2
(58) Field of Search .................. 119/417–420, 6.5, 119/712; 449/2, 1; 435/287.1, 288.7, 4, 29; 436/63; 422/98; 424/9.1; 73/866

(56) References Cited

U.S. PATENT DOCUMENTS

| | | | | |
|---|---|---|---|---|
| 3,367,308 A | * | 2/1968 | Quattrone et al. | 119/420 |
| 4,022,054 A | * | 5/1977 | Biederman | 73/23.34 |
| 4,807,706 A | * | 2/1989 | Lambertsen et al. | 169/45 |
| 4,969,417 A | * | 11/1990 | Sakano | 119/421 |
| 5,134,892 A | * | 8/1992 | Wilson et al. | 73/866 |

FOREIGN PATENT DOCUMENTS

JP 61083964 A * 4/1986 ............ G01N/33/48

OTHER PUBLICATIONS

Hammer et al."Learning and Memory in the Honeybee." The Journal of Neuroscience. vol. 15, No. 3 (Mar. 1995), pp. 1617–1630.*

Margaing et al."Effect of the concentration and nature of olfactory stimuli on the proboscis extension of conditioned honey bees *Apis mellifica ligustica*." Journal of Insect Physiology. vol. 35, No. 12 (1989), pp. 949–955.*

Sudduth, K.A., et al., "Sensors for Site–Specific Management", pp. 183–210. In Perce, F.J., and Sadler, E.J. (Eds.) The State of Site Specific Management for Agriculture. Amer. Soc. Agri. Inc., Madison, WI., 1997.

Gould, J.L., "Natural History of Honey Bee Learning", pp. 149–180, Dept. of Biology, Princeton University, Princeton, NJ 08544, USA, no date provided.

(Continued)

*Primary Examiner*—William H. Beisner
(74) *Attorney, Agent, or Firm*—John D. Fado; Gail E. Poulos

(57) ABSTRACT

A Chemical Detector, a training method and a method for detecting a chemical or chemicals has been developed that uses invertebrate organisms trained to respond to targeted chemical odors.

14 Claims, 18 Drawing Sheets

OTHER PUBLICATIONS

Bitterman, M.E., et al., "Classical Conditioning of Proboscis Extension in Honeybees (*Apis mellifera*)", *Journal of Comparative Psychology*, vol. 97(2), pp. 107–119, 1983.

Turlings, T.C.J.,et al., "Learning of Host–Findings Cues by Hymenopterous Parasitoids", pp. 51–78. In Papaj, D.R., and Lewis, A.C. (Eds.), Insect Learning. Ecological and Evolutionary Perspectives. Chapman & Hall, New York, no date provided.

Lewis, W.J., et al., "Host Detection by Chemically Mediated Associative Learning in a Parasitic Wasp", *Nature*, vol. 331, pp. 257–259, 1988.

Menzel, R., et al., "Biology of Invertebrate Learning", In Marler, P., and Terrace, H.S., (Eds.), The Biology of Learning. Springer–Verlag, Berlin, pp. 249–270, 1984.

Perez–Maluf, R., et al., "Genetic Variability of Conditioned Probing Responses to a Fruit Odor In *Leptopilina boulardi* (*Hymenoptera: Eucoilidae*), a *Drosophila* Parasitoid", *Behavior Genetics*, vol. 28(1), pp. 67–73, 1998.

Brandes, C., et al., "Common Mechanisms in Probiscus Extension Conditions and Visual Learning Revealed by Genetic Selection in Honeybees(*Aphis melifera capenis*)",*J. Comp. Physiol. A.*, vol. 166, pp. 545–552, 1990.

Heinrich, B., "Learning in Invertebrates", Dept. of Zoology, University of Vermont, Burlington, VT 05405, USA, no date provided.

Alloway, T.M., "Learning and Memory in Insects", *Annu. Rev. Entomol.*, vol. 17, pp. 43–56, 1972.

Papaj, D.R., et al., "Ecological and Evolutionary aspects of Learning in Phytophagous Insects", *Ann. Rev. Entomol.*, vol. 34, pp. 315–350, 1989.

Tumlinson, J.H., et al., "How Parasitic Wasps Find Their Hosts", *Scientific American*, pp. 100–106, Mar., 1993.

Lunau, K., et al., "Optical Releasers of the Innate Probiscis Extension in the *Hoverfly Eristalis tenax* L.(*Syrphidae, Diptera*)", *J. Comp. Physiol. A.*, vol. 174, pp. 575–579, 1994.

Wackers, F.L., "The Effect of Food Deprivationon the Innate Visual and Olfactory Preferences in the Parasitoid *Cotesia rubecula*", *J. Insect Physiol.*, vol. 40(8), pp. 641–649, 1994.

Gould, J.L., "Natural History of Honey Bee Learning", pp. 149–180, Dept. of Biology, Princeton University, Princeton, NJ 08544, USA.

Turlings, T.C.J.,et al., "Learning of Host–Findings Cues by Hymenopterous Parasitoids", pp. 51–78. In Papaj, D.R., and Lewis, A.C. (Eds.), Insect Learning. Ecological and Evolutionary Perspectives. Chapman & Hall, New York.

Heinrich, B., "Learning in Invertebrates", Dept. of Zoology, University of Vermont, Burlington, VT 05405, USA.

Lunau, K., et al., "Optical Releasers of the Innate Proboscis Extension in the *Hoverfly Eristalis tenax* L.(Syrphidae, Diptera)", *J. Comp. Physiol. A.*, vol. 174, pp. 575–579, 1994.

* cited by examiner

UTILIZATION OF INVERTEBRATE LEARNING FOR FLEXIBLE AND SENSITIVE MONITORING AND IDENTIFICATION OF CHEMICALS

CROSS REFERENCE TO PROVISIONAL APPLICATION

This application claims benefit of provisional application Ser. No. 60/195,218, filed Apr. 7, 2000.

BACKGROUND OF THE INVENTION

1. Field of the Invention

The present invention relates to a chemical detection system for chemical monitoring and/or identification using invertebrates, especially insects. It also relates to a method for training invertebrates to detect at least one chemical, a method for training insects to display response behaviors associated with close range biological cues in a non-biological setting in response to a chemical odor as well as to the trained invertebrates used in the system.

2. Description of the Related Art

Detector systems have played an integral and beneficial role in our culture for many years. Governmental institutions, medicine, agriculture, education, industry, and households rely on chemical and physical detectors for safety, quality control, research and communication. Gas chromatography and mass spectrometry have advanced the understanding of chemistry and the ecology and physiology of species (Olson et al., Physiol. Entomol., 1999, in press; Pare et al., Plant Physiol., Volume 114, 1161–1167, 1997), and x-rays and laser imaging have provided a means for detecting pathologies (Boice et al., JAMA, Volume 265, 1290–1294, 1991; Graham-Rowe, New Scientist, Volume 159, 24, 1998), including the quality of foods (Price et al., Food Technology, Volume 44, 6, 1990). Radar sensors are used internationally for communication, navigation, and entertainment (Galatie et al., Iee Proceedings-PADAR, SONAR and Navigation, Volume 144, 156–162, 1997) and Doppler radar systems monitor global weather patterns (Condella, Earth, Volume 7, 56–58, 1998). Near-infrared detectors monitor general vegetation health in agricultural systems (Bosch, Precision Farming: 20–24, 1997), accelerometers are used in cars to detect crash and signal deployment of airbags, and detectors are installed in homes to indicate the presence of harmful radiation, chemicals, and smoke (Edgerton et al., Environ. Science & Technology, Volume 20, 803–807, 1986; Lamarine et al., J. Community Health, Volume 17, 291–401, 1992).

Many of our technological developments have already been adapted from nature, for example, sonar, gyroscopes, heating and air conditioning, aviation, polyester, etc. (Au, Bioacoustics, Volume 8, 137–162, 1997; Engels et al., Studies on Neotropical Fauna and Environment, Volume 30, 193–205, 1995; Sherman, Agricultural Research, Volume 37, 18, 1989). However, with the exception of capturing the bioluminescence of fireflies, beeswax from bees, and the use of domestic animals as detectors (Cherfas, New Scientist, Volume 122, 45, 1989; King et al., Nature, Volume 249, 778–781, 1990), reliance on nature as models for technological development has been generally lacking. Only recently are investigations in the areas of robotics and biomimetics (Goldner, R & D Magazine, Volume 35, 77, 1993; Shimozawa, Rob. Autom. Syst., Volume 18, 75–82, 1996; Srinivasan, Materials Science & Engineering C-biomimetic Materials Sensors and Systems, Volume 4, 19–26, 1996; Weibecker et al., Talanta, Volume 44, 2217–2224, 1997) discovering nature's potential as models for technological development.

Domesticated animals, particularly dogs, have been relied upon as detectors. Historically, humans and domesticated animals have had a close association and many of these species have an incredible ability to detect objects and scents. Humans have been able to harness these abilities largely through training because of their ability to learn. Dogs have been successfully trained to detect narcotics, accelerants used in arson, and explosives, including landmines, and to track game and missing persons in search and rescue operations. How the learning process and human relationship with these domesticated animals works to create the responses to trained stimuli has never been totally understood. It is known that these animals often traverse and operate as effective detectors in less natural arenas, possibly because their historic domesticity has allowed them many years of adaptation to these environments. This ability has provided us with a means to utilize these trained and reliable detectors for our benefit in many different environments.

Although existing chemical detectors are specific and reliable and have allowed major advances in our ability to monitor systems, there remains a need in the art for chemical detector systems that have sensitivity, programmability, portability, and a cryptic nature that are needed for many current problems requiring detection and monitoring. The present invention provides a system and method of chemical detection which is different from prior art methods.

SUMMARY OF THE INVENTION

It is therefore an object of the present invention to provide a detection system containing a trained invertebrate organism for identification of target chemicals.

Another object of the present invention is to provide a detection system that includes at least one detection chamber containing at least one trained invertebrate organism and an air system.

A still further object of the present invention is to provide a detection system that includes a sensor located in a detection chamber for detecting the response of at least one trained organism to at least one target chemical.

A still further object of the present invention is to provide a method for recording at least one response of at least one trained organism to at least one target chemical.

Another object of the present invention is to provide a trained invertebrate organism.

A still further object of the present invention is to provide a method for training an invertebrate organism which includes placing the invertebrate in the immediate presence of a biological resource, such as for example, a host, mate, prey or food, etc., while smelling a target odor for at least about two times to train the organism to display a recordable response behavior, usually displayed in response to a close range biological cue, to a target chemical in a non-biological setting.

Another object of the present invention is to provide a method for detecting target chemicals which includes training an invertebrate organism to display a typical behavior in response to the smell of a target chemical, placing at least one trained organism in at least one detection chamber compartment containing a divider with an opening containing a sensor, attaching this to an air system, pumping air from the suspected area through the detection chamber and recording the organisms behavior, and exhausting the test air.

Further objects and advantages of the invention will become apparent from the following description.

BRIEF DESCRIPTION OF THE DRAWINGS

FIG. 9 is a photograph of *M. croceipes* exhibiting head-sticking behavior when presented with the learned target odor in the absence of food, trained females attempt to enter the hole where the odor is emanating from.

DETAILED DESCRIPTION OF THE INVENTION

Figure 1:
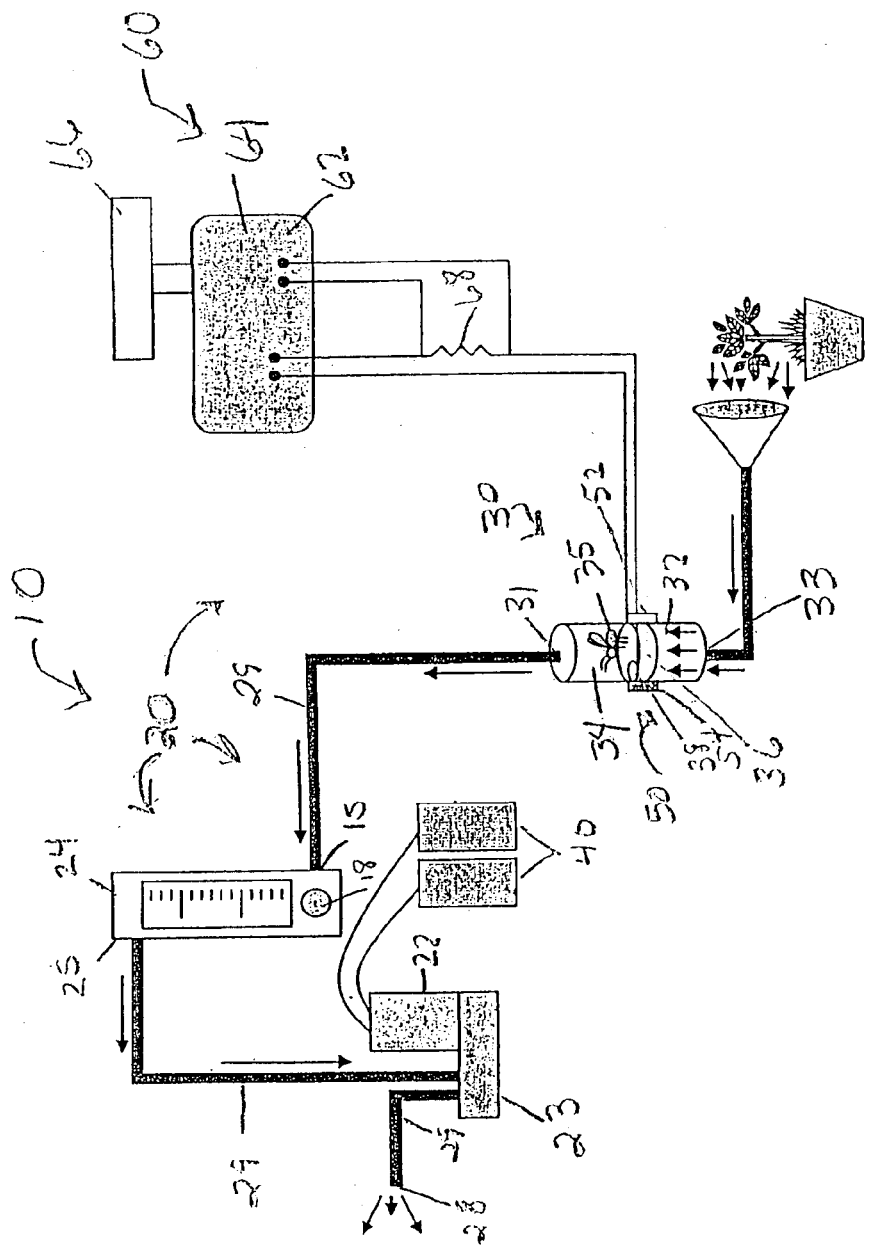
FIG. 1 is a schematic drawing of a portable chemical detection device.
Figure 2:
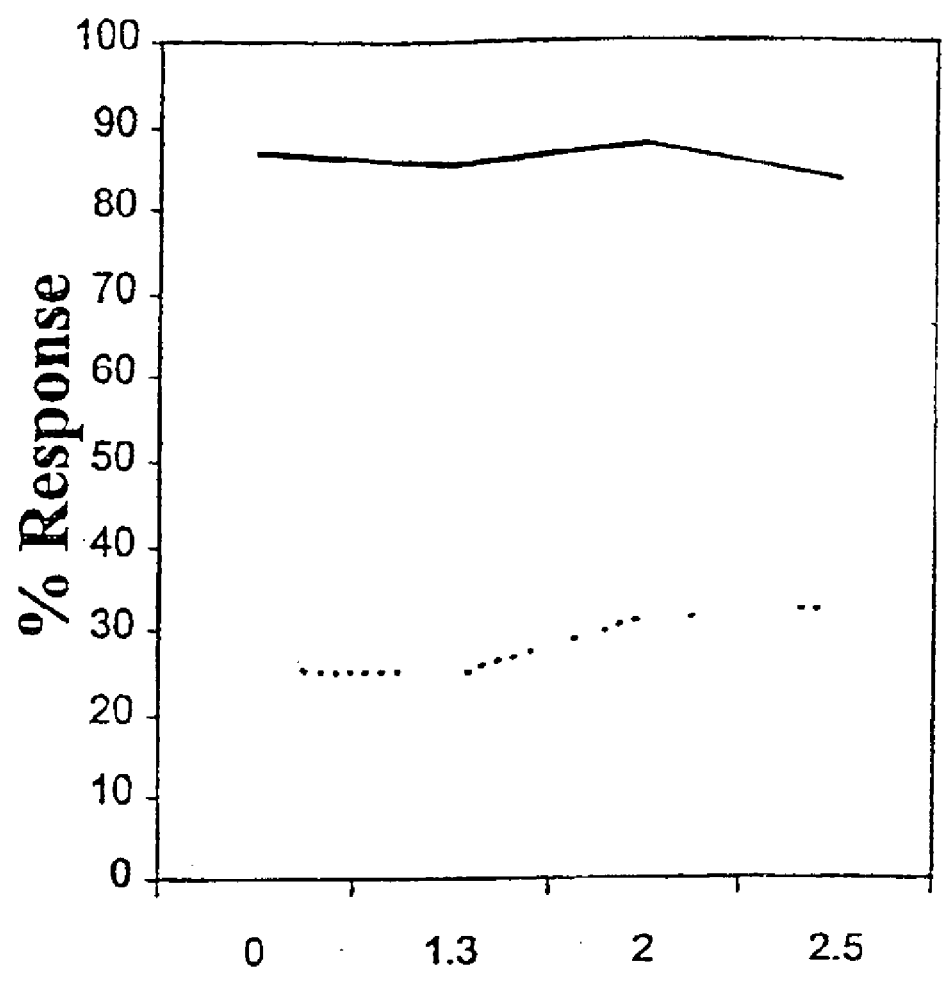
FIG. 2 is a graph showing % flight response of experienced and inexperienced female *Microplitis croceipes* to Trans-caryophyllene at about 1,20, 100 and 300 ng/minute release rate. N=about 145 experienced and about 147 inexperienced females.
Figure 3:
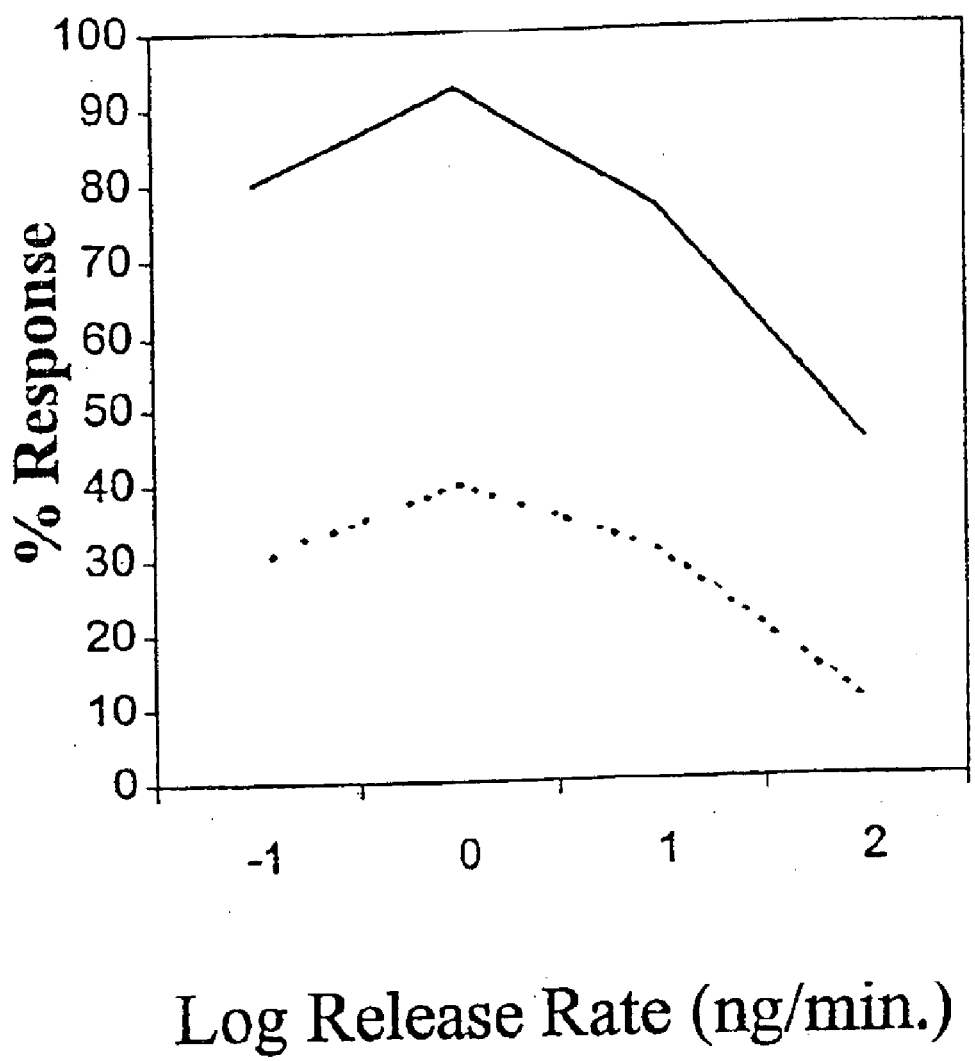
FIG. 3 is a graph showing % flight response of experienced and inexperienced female *Microplitis croceipes* to methyl jasmonate at about 0.05,1,10, and 100 ng/minute release rate. N=about 200 experienced and inexperienced females.
Figure 4:
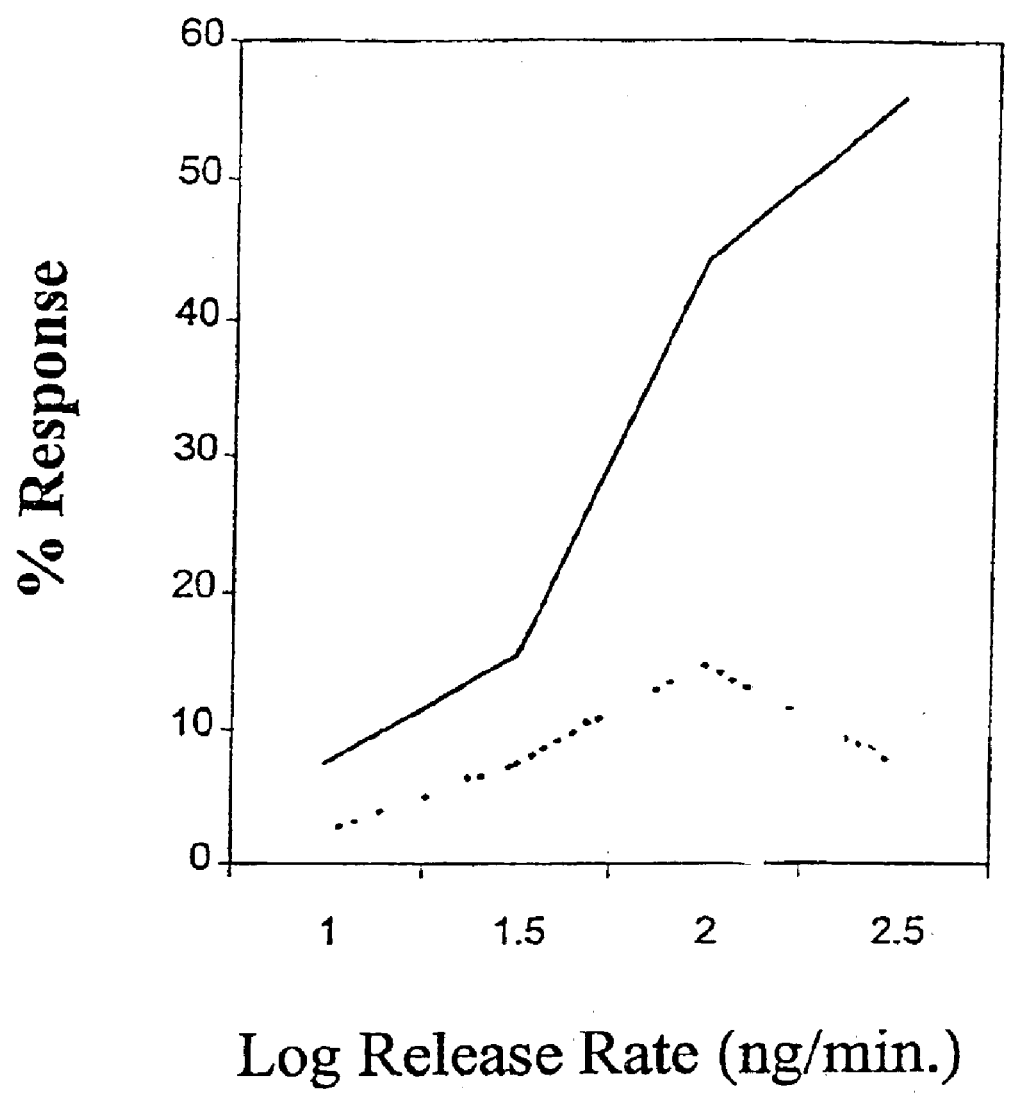
FIG. 4 is a graph showing % flight response of experienced and inexperienced female *Microplitis croceipes* to cyclohexanone at about 10, 30, 100 and 300 ng/minute release rate. N=about 162 experienced and about 157 inexperienced females.

Invertebrate organisms can be used as highly flexible and sensitive detectors in a system for chemical monitoring and/or detection. The three major areas which benefit from a sensitive, portable, cryptic and reliable detection system include agriculture, national defense, and medicine.

There is a growing need for more sensitive, programmable, portable, and cryptic detector systems. A contained invertebrate organism, such as an insect, provides two means for retrieving information. First, the organism interprets and expresses behavior(s) in response to the presence of a chemical. The expressed behavior(s) is distinct, i.e. easily recognized, and is a reliable indicator of the presence of a chemical. The organism must remain focused and is not easily distracted. Second, the sensory apparatus, such as antennae, antennae lobe or brain for example, of the contained organism can be tapped into to obtain the response. Both avenues require that the organism be delivered to the source or the source be delivered to the organism and monitored by an individual or the processed information analyzed by a programmed computer. The present invention can be used in easily accessible areas, such as for example, airports, agricultural fields, hospitals, etc.

In agriculture, the detectors of the present invention will allow plant and soil health to be monitored as well as interaction of species which leads to early problem detection and intervention. Current technology, using remote sensing systems, cannot immediately detect specific nutrient levels or early stages of pest infestations, and large and expensive gas chromatography and optical and mass spectrometry equipment cannot be taken to the field, which limits diagnosis to a few transported samples. In addition, small, rugged, and inexpensive solid state chemosensors, like metal doped $SnO_2$-sensors, lack the sensitivity and selectivity that is necessary.

In the area of national defense for chemical and biological weapons detection, bio-weapons cannot be detected with radiation or x-ray, making them well concealed and easily transported for release into transit, water and food systems. Medical centers are not prepared for the delays inherent in recognizing that a bio-weapon has been released. There is a need for new technology for rapid and sensitive weapon detection, including the need for more cryptic means of detection in adversarial zones.

In medicine, there is a need for less invasive detection of pathogens and monitoring of human and animal health. Recent studies show that dogs can be trained to noninvasively detect screwworm infested animals and breath analysis can detect peptic ulcer disease, both procedures eliminating the need for painful endoscopic examinations.

The present invention separates a very specific behavior from its biological context for use as a reporting device, called a response behavior. This response behavior is defined for purposes of the present invention as any behavior the organism usually displays when in close proximity to a biological resource such as, for example, food, mate, prey, or host. This response behavior can be isolated from the organism's natural behavioral context and used with any chemical cue using the training method of the present invention. The method of the present invention quickly programs the organisms in at least about 1 minute to about 4 hours and brings the organisms to report trained odors, especially odors not related to the biology of the organism, with high accuracy under a wide range of environmental conditions. The trained organisms can pick out a single chemical from a chemical blend after being trained to a mix containing that chemical. In the present invention, knowledge of the chemical nature of the programmed odors is not necessary.

This invention recognizes the potential of invertebrates, especially insects, in chemical detection systems. Insects have experienced intense selection pressure for sensitive and effective ability to locate mates, food and hosts in nature. For example, *Microplitis croceipes* Cresson are endoparasitoids of the larvae of *Heliocoverpa zea* Boddie and are able to detect and respond to volatile chemicals from host plant sources in amounts as low as $4.5 \times 10^{-16}$ M. Such low detection thresholds are comparable to those of vertebrates (Smith et al., Annu. Rev. Entomol., Volume 39, 351–375, 1995; Stoddart, In: The Ecology of Vertebrate Olfaction, 58–62, 1980, Chapman and Hall, New York, N.Y.). Insects are able to learn which allows them to be programmable. Only recently the breadth of insects learning abilities has been discovered (Papaj et al., In. Insect Learning. Ecological and Evolutionary Perspectives. Chapman and Hall, 1993; Vet et al., In: Chemical Ecology of Insects 2, 65–101, 1995, Chapman and Hall, New York, N.Y.). Invertebrates have a very short generation time and they can be easily reared in large numbers. The great diversity of insects allow different species to be drawn upon for use in specific habitats or environments.

The trained organisms of the present invention can be used with any type of device which will allow a behavioral response to be recorded. It is preferred that the device is portable. At a minimum the device needs a means for introducing a sample of air from a suspected area into at least one detection chamber containing at least one trained organism. One example of a chemical detection device containing a trained organism is illustrated in FIG. 1. Device 10 is a programmable, portable, and cryptic detector system for detecting at least one chemical such as for example those contained in explosives, those associated with microorganism contamination, those associated with parasitic contamination, those associated with various contraband, etc. Components of detector 10 include an air system 20, at least one detection chamber 30, a power source 40, and a sensor means 50 with data analysis system 60. The analysis of the information received from the sensor can be performed on (a) a computer with one computer parallel port input line interfacing with each sensor, (b) a computer with a commercial digital I/O computer board for applications requiring more than eight sensors, (c) dedicated memory registers with a control/display unit, (d) commercial controller and datalogger wth the ability to read analog input channels and output analog or digital data, with a display unit, microcontroller with display unit, etc.

Detector 10 has an air system 20 which pumps the air to be tested into the system and exhausts it. Air system 20 includes an air pump 22, air flow control valve and meter 24, an air sample inlet 26, an air sample exhaust 28 and tubing 29. Air pump 22 can be any pump with a motor. The type of air pump is determined by the amount of air that is desired to be drawn into the system and is readily determined by one of ordinary skill in the art. Typically, a micro-air pump and motor is used, for example a diaphargm pump with motor. Pump 22 is connected to the outlet end 25 of air flow control valve and meter 24 with tubing 29. Tubing 29 can be any thing which will contain flowing air. Typically tubing 29 is any tubing through which air can be pumped and does not absorb odors, such as for example TEFLON, glass, silicon, etc. Air flow valve and meter 24 is connected to the outlet end 31 of detection chamber 30 with tubing 29. The outlet end 23 of pump 22 is the pump exhaust port which forms air sample exhaust 28. Chamber 30 is connected through its inlet end 33 to air inlet 26 with tubing 29. Air inlet 26 includes an air intake unit 27 with an inlet 21 and an outlet 23 end. Unit 27 can be of any size or shape which is determined by the type of sampling to be done, determination of which is within the ordinary skill of the art. Typically, unit 27 is funnel-shaped. Unit 27 is connected by tubing 29 at its outlet end 23 to the inlet end 33 of at least one chamber 30. Unit 27 can be any material which is compatible with the air being sampled and does not absorb odors, such as for example, teflon, glass, etc. Determination of useful materials for unit 27 is well within the ordinary skill in the art. For multiple chamber systems, flow rate is increased by flow control valve 18 on the air control valve and meter 24.

Power source 40 is connected to pump 22. Power source 40 can be anything which operates the air pump. For portability it is preferred to use batteries for power source 30. The size and number of batteries is determined by the size of the air pump used and is readily determined by one of ordinary skill in art.

Detection chamber 30 is constructed of light weight transparent material such as for example, a plastic or other suitably durable material, such as for example, glass, acrylic, etc., which allows viewing of trained organism 35 and does not absorb odor. The chamber contains at least two compartments, air sample compartment 32 and trained organism compartment 34, separated by divider 36. Air flows from the air sample inlet 26 to compartment 32. Divider 36 separates compartment 32 from compartment 34 and contains an opening 38 which allows air communication between the two chambers. Divider 36 can be of any size which fits chamber 30 and provides an opening containing a sensor. Opening 38 is only large enough to allow trained organism 35 to enter. Opening 38 is smaller at the compartment 32 entrance to prevent trained organism 35 from escaping the trained organism compartment 34. Embedded in the walls of opening 38 is a sensor means 50, typically an electronic sensor such as as one that includes a phototransistor 52 and IR LED 54, for example, which signals when an organism has entered opening 38, thus counting the entry as a positive response with a data analysis system 60. The data analysis system can include, for example, a CR-10 Controller 62 and Datalogger 64 and a digital display 66 connected to photoresistor 52 through a 1 kohm resistor 68. Sensor means 50 can be an infrared sensor, visible light, laser or other optical device. Sensor means 50 is connected to a data analysis system 60 such as (a) a computer with one computer parallel port input line interfacing with each sensor, (b) a computer with a commercial digital I/O computer board for applications requiring more than eight sensors, (c) dedicated memory registers with a control/display unit, (d) commercial controller and datalogger, with the ability to read anlog input channels and output analog or digital data, with a display unit, (e) microcontroller with a display unit, for example. Divider 36 can be made of any material, preferably a material which does not absorb odors, such as for example, teflon, acrylic, glass, etc. and is plug-shaped. Compartment 34 must be large enough to contain trained organism 35 and contains an outlet end 31 which is connected to the inlet end 15 of valve and meter 24 by tubing 29. The size of chamber 30 must be at least large enough to comfortably hold at least one trained organism and allow it to display the response behavior to which was trained in response to detection of the at least one chemical to which it is trained. The determination of the size and shape of chamber 30 and its compartments is within the ordinary skill in the art. Device 10 has at least one chamber 30 and can have as many as the desired application requires. Each chamber is connected to each other through outlet end 31 and inlet end 33 with tubing 29. Each chamber contains at least one organism trained to at least one chemical. With multiple chambers, each chamber can contain at least one organism trained to the same target chemical when it is desired to obtain a response requiring a required percentage for a positive response. In other instances, each chamber can contain at least one organism trained to a target chemical different from the target chemical detected by the other chambers. This is useful when the detection system is being used to monitor several different chemicals in the same location.

In operation, air pump 22 pulls air to be sampled into air inlet 21 to at least one compartment 32 of at least one chamber 30. Air flow is controlled by flow control valve 18 of air control valve and meter 24. As the air enters chamber 34 through opening 38, it passes at least one trained organism 35. If the sampled air contains the chemical or chemicals to which organism 35 is trained, organism 35 will move into opening 38 disrupting the sensor means 50 signal. In FIG. 1, by way of example, the trained organism enters opening 38 breaking an infrared beam which turns photoresistor 52 on and off and changes the voltage drop across resistor 68 in the circuit. The voltage change is measured with a Campbell CR-10 controller 62 and datalogger 64. The CR-10 measures the voltage about every $\frac{1}{8}$ second and displays the number of times the beam is broken about every two seconds on digital display 66. The sampled air exits the at least one chamber 30 and enters tube 29, flows through air control valve and meter 24 through inlet end 15 and exits at outlet end 25. It continues to air sample exhaust 28 through pump 22 where it exits the device.

The training method of the present invention is useful for training invertebrates. For purposes of the present invention, invertebrates include, for example, Arthropods, including but not limited to wasps, bees, moths, butterflies, beetles, true bugs (e.g. assasin bugs); and arachnids, for example, including but not limited to spiders, mites, ticks, and scorpions; Crustacians, for example, including but not limited to crayfish, lobster, and crabs; and mollusks, for example, including but not limited to snails, slugs, squids, and clams.

A naive invertebrate organism is placed in the immediate presence of a biological resource such as a close range biological resource, such as for example, a host, mate, prey or food, while smelling a target chemical until the organism displays the response behavior typical to that close range biological cue. For purposes of the present invention, a biological resource is any resource where the organism will immediately take action such as for example stinging a host, eating, mating, harvesting prey, etc. Immediately upon display of the response behavior, the organism is removed from the biological resource. This step is repeated at about 2 times every few seconds up to about every 60 minutes. For a food source, the organism is allowed to feed for a few seconds, removed from food, and then allowed to feed again. The organism is then trained. For a host source, the organism is allowed to attack the host once, it is removed and then about 30 to 60 minutes later it is put back with the host again. This step can be repeated 2–3 times. The target chemical can be directly applied to a biological cue such as a host, the target chemical can be on a piece of paper that is placed close to the organism when contacting the biological resource, it can be placed downwind from the organism with air drawn past the chemical to the organism while it is contacting a biological resource, etc.

Response behaviors include but are not limited to for example:

(A) Attack postures such as in insects—coiling, stinging; in crustacian and mollusk appendage extension/grabbing movement;

(B) Oriented movement such as flying, walking, jumping, crawling, etc.;

(C) foraging behavior such as in insects anntenating, head-sticking, uncoiling of proboscis; in crustacians and mollusks appendage movement such as digging, extensions from shell, etc.

Next, a trained organism is placed near the target chemical without a biological cue, such as a food or host source for example, to confirm that the organism is displaying the response behavior associated with the biological in response to the target chemical with no biological cue. The trained organism is then placed into detector chamber compartment 34 as described above. For purposes of the present invention, a target chemical is any chemical for which there is a need to detect. These include but are not limited to chemical odors released by (a) contaminating microorganisms on crops, agricultural commodities, in livestock, in humans, in bioweapons, etc., (b) explosives, (c) accelerants, (d) drugs, (e) contraband, etc.

The detection system with at least one trained organism is then placed in an area suspected of containing at least one target chemical. Air is pumped from the air suspected of having the at least one target chemical into the system, past the at least one organism. If response behavior is displayed, a sensor will be tripped and a positive response will be recorded. The sample air is then exhausted from the system and the system purged with clean air. The at least one trained organism will remain trained for about 48 hours before retraining or replacement.

The parasitic wasp, *Microplitis croceipes*, is used as a model organism, to show trained organisms in a system for chemical detection. *Microplitis croceipes* (Cresson) (Hymenoptera:Braconidae) is a solitary larval parasitoid of *Heliothis* and *Helicoverpa* species (Hymenoptera:Noctuidae). Adult females forage for food and hosts according to their physiological needs and females may use learned odors to locate both resources. Thus, females with experience on a plant-host complex or on host frass (faeces) are attracted to the odor of the plant-host complex and to host frass odor. Naive females antennating host frass link its odor with a nonvolatile recognition kairomone found in frass that reinforces associative learning. In that manner, wasps learn odors associated with the presence of hosts and subsequently use these odors as cues while foraging for more hosts. Wasps are readily conditioned to fly, coil, head-stick or antennate in response to odors associated with a host or food source.

The following examples illustrate the use of a chemical detection system using *Microplitis croceipes* as a test model.

The examples are intended to further illustrate the invention and are not intended to limit the scope of the invention defined by the claims.

EXAMPLE 1

The insects used in the following examples were laboratory reared at about 28° C. and about 50–70% relative humidity, with a 16:8 light cycle. Larvae of *Heliothis zea* were reared on pinto bean artificial diet according to the method described by Burton (U.S.D.A. Tech. Bull. ARS SER. 33/134, 1969; herein incorporated by reference). *Microplitis croceipes* were reared on *H. zea* as described by Lewis and Burton (Ann. Entomol. Soc. Amer., Volume 64, 471–473, 1970; herein incorporated by reference). Adult wasps were held in Plexiglas cages provided with water and honey. In all experiments females wasps were about 2–6 days old and host larvae were about $2^{nd}$ and $3^{rd}$ instar. Each experiment was completed over about 2 to 5 days with females from different cohorts each day. Each day, the same number of wasps was used for all treatments within an experiment.

EXAMPLE 2

Female *M. croceipes*, about 2–4 days old were starved (provided water only) for about 26 to 30 hours at the time of the bioassays described below. The wasps were trained to detect trans-caryophyllene and methyl jasmonate which are two plant compounds; cyclohexanone which is a component of explosives; and diisopropyl-amino-ethanol which is a component of a neural toxin. These compounds were placed in capillary tubes that varied in diameter and the length of the tube above the meniscus of the solution to vary the release rates of the compounds. This procedure followed a modification of Stephan's Law:

$$Q=DAC/L$$

whereby the release rate Q is derived from D, a diffusion constant specific to the compound, A the cross-sectional area of the capillary tube, C the concentration gradient and L the length of the vapor column. The dimensions and formulations for the tubes are listed in Table 1 below. For about 3, 30, and 300 ng/minute release rates, 3 tubes at about 1, 10, and 100 ng/min were combined. The tubes were placed in a vertical position in a stand and centered in front of a 5 mm diameter glass tube positioned so that air flowed over the top of the capillary tubes containing the chemicals and vapors moved horizontally through the flight tunnel. The glass tube was attached to a generator and an air flow meter with plastic tubing threaded through a hole in the floor of the flight tunnel. Airflow over the capillary tubes was approximately 50 ml/minute and the wind tunnel air speed was about 60 cm/second for all chemicals tested. To train the wasps, an approximately 200 μl capillary tube (D=1.682) with one end sealed was filled with the source chemical so that the length of the vapor column was about 1–2 mm. The capillary tube was positioned upright through a PTFE/silicon septa attached to a glass T-tube (Wheaton) in a training apparatus where the air flows over the top of the capillary tube, down a glass rod and into a glass petri dish where the wasps are trained.

About a 10 μl drop of an approximately 50% sucrose (about 99% pure)/DI water solution was placed near the center of the glass petri dish and wasps were allowed to feed for about 5 seconds while the vapor from the chemical was gently blown over the antennae of the wasp. This procedure was repeated three times with about 30 second intervals. The protocol for inexperienced females was the same as for experienced females except that only air was blown over their antennae.

A single female was placed on a stand about 13 cm high and about 80 cm downwind of the chemical source so that she was within the plume of the chemical at take-off. The time it took for each inexperienced and experienced female to take-off and fly upwind and whether she landed on the source was recorded at each release rate. Females that did not complete a flight after three chances or that did not take-off after about 3 chances or did not take-off after about 5 minutes were scored as not successful. A total of about 8–10 females per treatment were assayed per day over about 4 days. The difference in the number of successful landings on the source between inexperienced and experienced females was determined with a Chi-square test. The results are shown in Table 2 below and FIGS. 1–4.

TABLE 1

Formulated release rates of compounds utilized in flight tunnel bioassays.

| Compound | D (mm) | L (mm) | Release rate (ng/min.) |
|---|---|---|---|
| Caryophyllene | 0.7 | 107 | 1.1 ± 0.6 |
|  | 1.682 | 60 | 25 ± 6 |
|  | 1.682 | 6 | 100 ± 20 |
| Methyl jasmonate | 1.682 | 90 | 0.025? |
|  | 1.682 | 45 | 0.05? |
|  | 1.682 | 14 | 0.10? |
|  | 1.682 | 5 | 1.4 ± 0.2 |
|  | 4 | 6 | 10 ± 2.2 |
|  | 4 | 4 | 100 ± 10 |
| Cyclohexanone | 0.755 | 630 | 9.25 ± .8 |
|  | 0.700 | 80 | 107 ± 8.5 |
| Diisopropylamino-ethanol | 0.700 | 30 | 0.05? |
|  | 0.700 | 15 | 1.8 ± .1 |
|  | 1.682 | 45 | 9.5 ± 3.2 |
|  | 1.682 | 10 | 78 ± 33 |

TABLE 2

Mean and SEM percentage of successful flights to trans-caryophyllene, methyl jasmonate, cyclohexanone and diisopropylamino-ethanol at various release rates for experienced and inexperienced females.

| Compound | N | Mean (SEM) | Release rate (ng/min.) |
|---|---|---|---|
| Trans-Caryophyllene |  |  |  |
| Experienced | 37 | 86.8 (2.3)*** | 1 |
| Inexperienced | 39 | 25.5 (2.6) | 1 |
| Experienced | 41 | 85.3 (3.0)*** | 30 |
| Inexperienced | 40 | 25.0 (6.4) | 30 |
| Experienced | 32 | 88.0 (0)*** | 100 |
| Inexperienced | 32 | 31.5 (3.8) | 100 |
| Experienced | 36 | 83.3 (3.5)*** | 300 |
| Inexperienced | 36 | 32.5 (6.0) | 300 |
| Methyl jasmonate |  |  |  |
| Experienced | 40 | 55.5 (5.0)* | 0.025 |
| Inexperienced | 40 | 20.0 (4.1) | 0.025 |
| Experienced | 40 | 40.0 (4.1)* | 0.05 |
| Inexperienced | 40 | 10.0 (0) | 0.05 |
| Experienced | 40 | 80.0 (0)*** | 0.10 |
| Inexperienced | 40 | 30.0 (4.1) | 0.10 |
| Experienced | 41 | 92.8 (2.4)*** | 1 |
| Inexperienced | 40 | 40.0 (10.8) | 1 |
| Experienced | 40 | 77.5 (2.5)*** | 3 |
| Inexperienced | 40 | 25.0 (6.4) | 3 |
| Experienced | 38 | 76.3 (2.4)*** | 10 |
| Inexperienced | 38 | 31.3 (6.6) | 10 |
| Experienced | 40 | 67.5 (2.5)*** | 30 |

TABLE 2-continued

Mean and SEM percentage of successful flights to trans-caryophyllene, methyl jasmonate, cyclohexanone and diisopropylamino-ethanol at various release rates for experienced and inexperienced females.

| Compound | N | Mean (SEM) | Release rate (ng/min.) |
|---|---|---|---|
| Inexperienced | 40 | 15.0 (2.9) | 30 |
| Experienced | 40 | 45.0 (6.5)*** | 100 |
| Inexperienced | 40 | 10.0 (4.1) | 100 |
| Cyclohexanone | | | |
| Experienced | 40 | 7.4 (2.5) | 10 |
| Inexperienced | 40 | 2.5 (2.5) | 10 |
| Experienced | 44 | 15.3 (3.0) | 30 |
| Inexperienced | 40 | 7.5 (4.8) | 30 |
| Experienced | 36 | 44.3 (8.9)* | 100 |
| Inexperienced | 36 | 12.9 (6.5) | 100 |
| Experienced | 43 | 55.8 (2.2)*** | 300 |
| Inexperienced | 41 | 7.5 (2.5) | 300 |
| Diisopropylamino-ethanol | | | |
| Experienced | 38 | 49.5 (4.5)* | 0.05 |
| Inexperienced | 38 | 2.5 (2.5) | 0.05 |
| Experienced | 41 | 41.8 (5.5)* | 1 |
| Inexperienced | 40 | 10.0 (4.1) | 1 |
| Experienced | 40 | 27.5 (2.5)* | 3 |
| Inexperienced | 40 | 7.5 (4.8) | 3 |
| Experienced | 40 | 30.0 (4.1)** | 10 |
| Inexperienced | 40 | 2.5 (2.5) | 10 |
| Experienced | 40 | 14.3 (4.8) | 100 |
| Inexperienced | 40 | 7.8 (2.8) | 100 |
| Experienced | 38 | 5.8 (3.4) | 300 |
| Inexperienced | 38 | 3.0 (3.3) | 300 |

$\chi^2$ $df_1$
***$p < 0.001$,
**$p < 0.01$,
*$P < 0.05$

EXAMPLE 3

Figure 5:
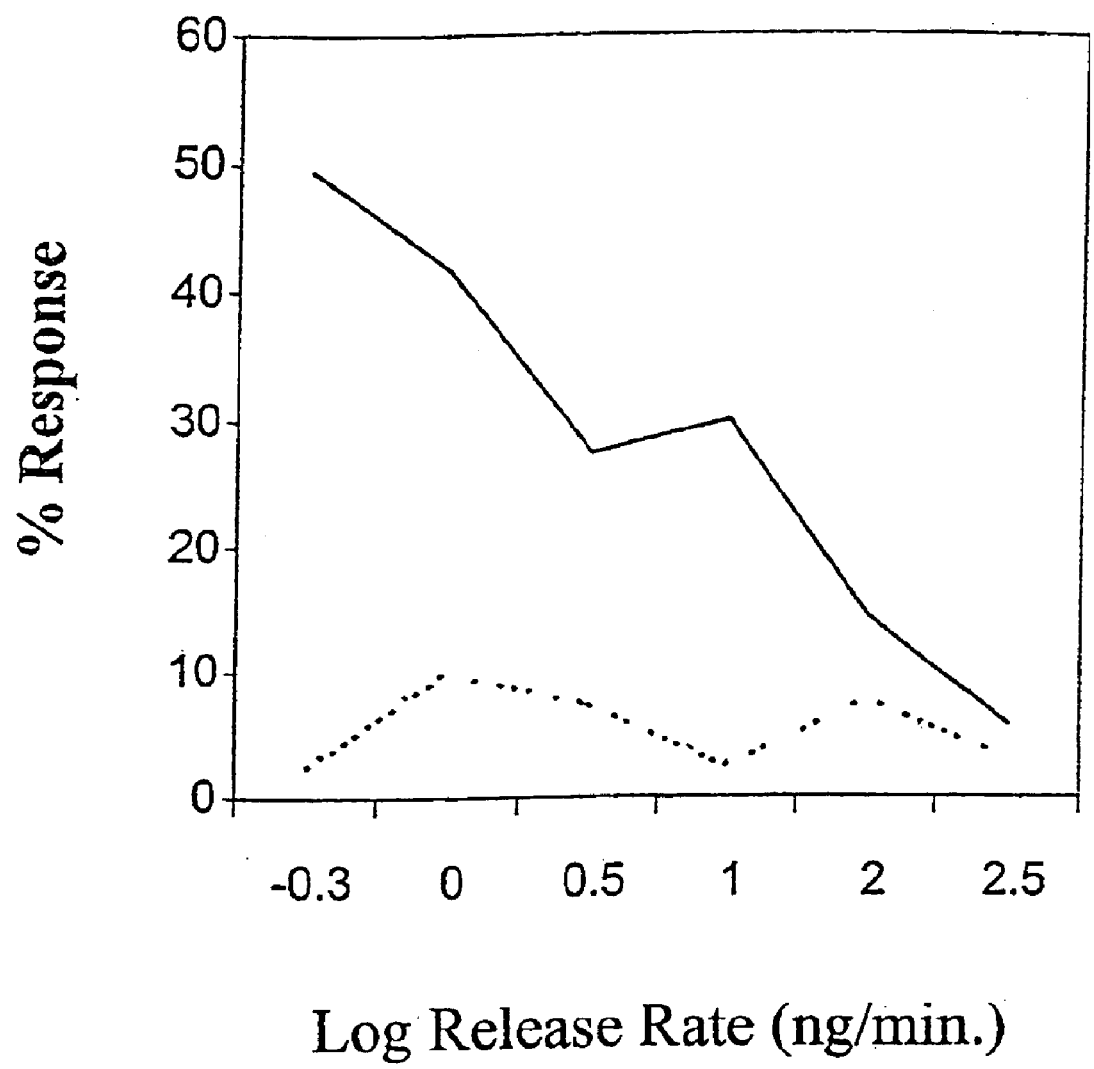
FIG. 5 is a graph showing %flight response of experienced and inexperienced female *Microplitis croceipes* to Diisopropyaminoethanol at about 0.5, 1,3,10,100 and 260 ng/minute release rate. N=about 237 experienced and 239 inexperienced females.

This example characterized the coiling behavioral response of wasps challenged in different ways after identical training. Both vanilla and orange aromas were used as target stimulus. After training, the 'close range' (Proximal) behavior was examined. About two hours after training, an approximately 20 μl pipet was presented to the wasps held individually in glass tubes (about 0.13×4.5 cm). The pipet was pointed towards the head of the insect and moved gently back and forth for about 2–5 seconds while the wasp's behavior was observed. Each wasp was tested about three times sequentially, first with a pipet dipped into the extract they experienced during the training phase (vanilla or orange), then with a pipet dipped into the alternative extract, and finally with a pipet dipped into the first extract. About half of the wasps of the control group were tested with vanilla first, the others were tested with orange first. Approximately ten minutes elapsed between tests. Upon presentation of a pipet, it was recorded whether the wasp showed coiling behavior. Coiling resembled the position usually assumed by wasps about to attack a larva: raised on hind legs facing the pipet, antennae held still with the terminal end of the flagellum bent down (FIG. 5). After coiling, wasps often jumped onto the pipet.

Before beginning the testing, in order to verify that wasps did not coil towards the pipet alone, wasps were challenged with a clean pipet. Coiling was observed only occasionally, about 8%. All wasps were challenged with a blank pipet until two negative responses (no coiling) were observed in a row (about 5 times maximum). This procedure was repeated after the first test with food extract to verify again that wasps did not coil to the pipet alone (about 3%).

Figure 6:
FIG. 6 is a photograph of *M. croceipes* exhibiting the coiling response behavior with a learned target odor in the absence of a host or food source.

About 77% of wasps trained with vanilla on larvae coiled towards the vanilla scented pipet compared to about 14% of the control wasps (See FIG. 6). These results demonstrate that coiling was due to the presence of vanilla and was a result of learning. On the contrary no wasps in either group coiled towards the orange-scented pipet whereas when these wasps were challenged again with the vanilla-scented pipet, about 58% of the vanilla group coiled compared with about 7% in the control group. These results indicate that the absence of coiling towards orange was not due to fatigue, habituation to the pipet test, negative learning or memory extinction, since wasps coiled towards the vanilla afterwards. Thus, coiling by vanilla-trained wasps was a response specific to vanilla and was acquired through learning.

Figure 7:
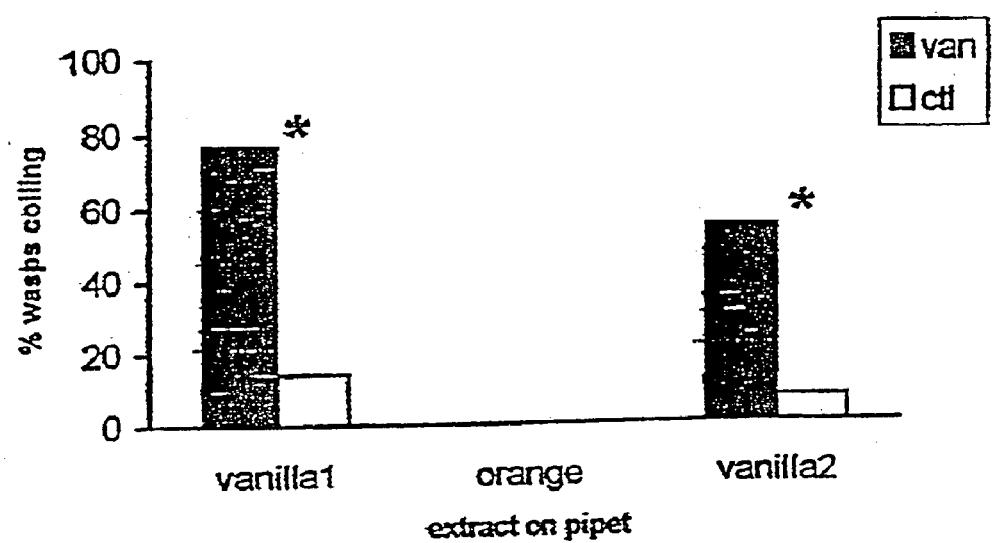
FIG. 7 is a graph showing percentage of female *M. croceipes* coiling towards three pipets presented successively scented with vanilla or orange extract (left to right). Wasps previously had 3 oviposition experiences on hosts scented with vanilla (van) or on clean hosts (ctl). Stars indicate results significantly different between vanilla and control (Fisher's exact test, $\alpha>0.05$).

Similarly, about 59% of wasps trained with orange coiled towards the orange-scented pipet while none of the control group did (See FIG. 7). No wasp coiled towards the vanilla-scented pipet and about 56% of the orange-trained wasps coiled towards the orange-scented pipet the second time. Thus, coiling by orange-trained wasps was a response specific to orange and was acquired through learning.

EXAMPLE 4

Figure 8:
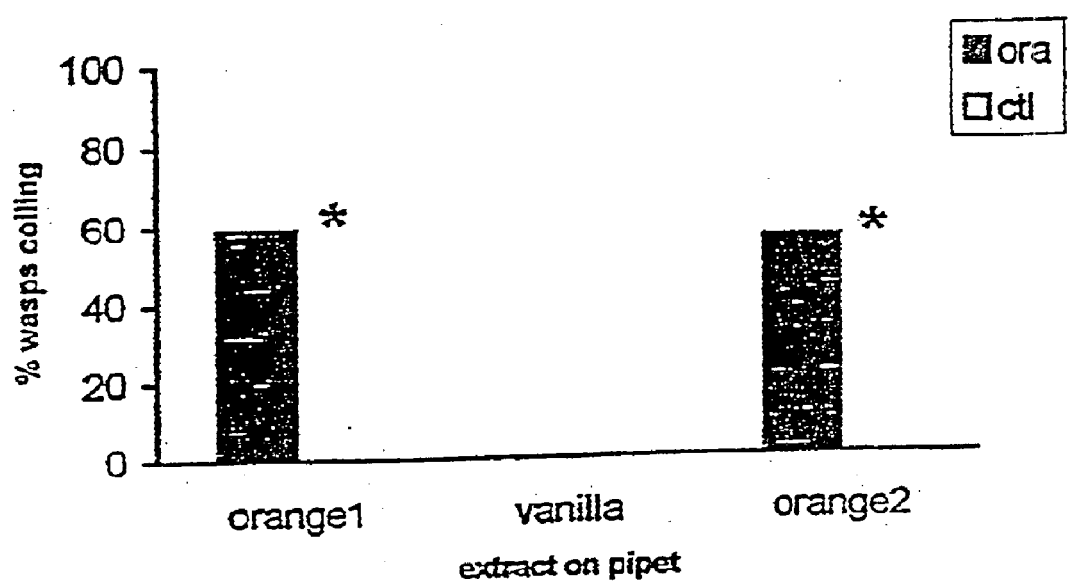
FIG. 8 is a graph showing percentage of female *M. croceipes* coiling towards three pipets presented successively scented with vanilla or orange extract (left to right). Wasps previously had 3 oviposition experiences on hosts scented with orange(ora) or on clean hosts (ctl). Stars indicate results significantly different between orange and control (Fisher's exact test, $\alpha>0.05$).

Male and female *M. croceipes* were used to demonstrate the head-sticking response of the wasps using 3-Octanone. Head-sticking behavior is when a wasp sticks its head into an opening from which is emanating a target chemical odor (FIG. 8). The wasp attempts to enter the opening from which the odor is emanating For training, males were given only water for abut 24 hours and females for about 48 hours as described above in example 2. 3-Octanone diffused from several holes surrounding a saturated filter paper containing about a 50% sucrose-water solution. Wasps were allowed to feed for about 10 seconds about 3 times about every 30 seconds. Control wasps were given the sucrose-water solution without an odor source.

Figure 9:

Trained and control wasps were then placed on the divider of a detection chamber where the source chemical emanated from the opening. The percentage of wasps entering the opening was recorded for about 40 male and female wasps per release rate of aobut 0.8 and 33.3 ng/minute of 3-Octanone. The results are shown in FIG. 9. The control wasps showed no head-sticking behavior in response to 3-Octanone and between about 78% to about 99% of female and male wasps responded to 3-Octanone with head-sticking behavior.

EXAMPLE 5

Female *M. croceipes* were trained to detect white mold, *Sclerotium rolfsii*, which causes plant wilt and effects fruit development on plants such as peanuts, using the method outlined in Example 3 for coiling behavior and example 4 for head-sticking behavior. Coiling responses after training with white mold or air only indicates that wasps can detect white mold in a complex chemical background. The trained wasps were exposed to white mold on agar, uncontaminated peanuts, and white mold on peanuts. Approximately 50% of the mold-trained wasps coiled when exposed to white mold on agar as compared to approximately 5% response from the untrained wasps. There was no significant difference between trained and untrained wasps exposed to peanuts with about 25–30% of each group coiling. About 60% of the trained wasps coiled when exposed to white mold on peanuts compared to untrained wasps which coiled approximately 30% (See FIGS. 5 and 10).

Figure 10:
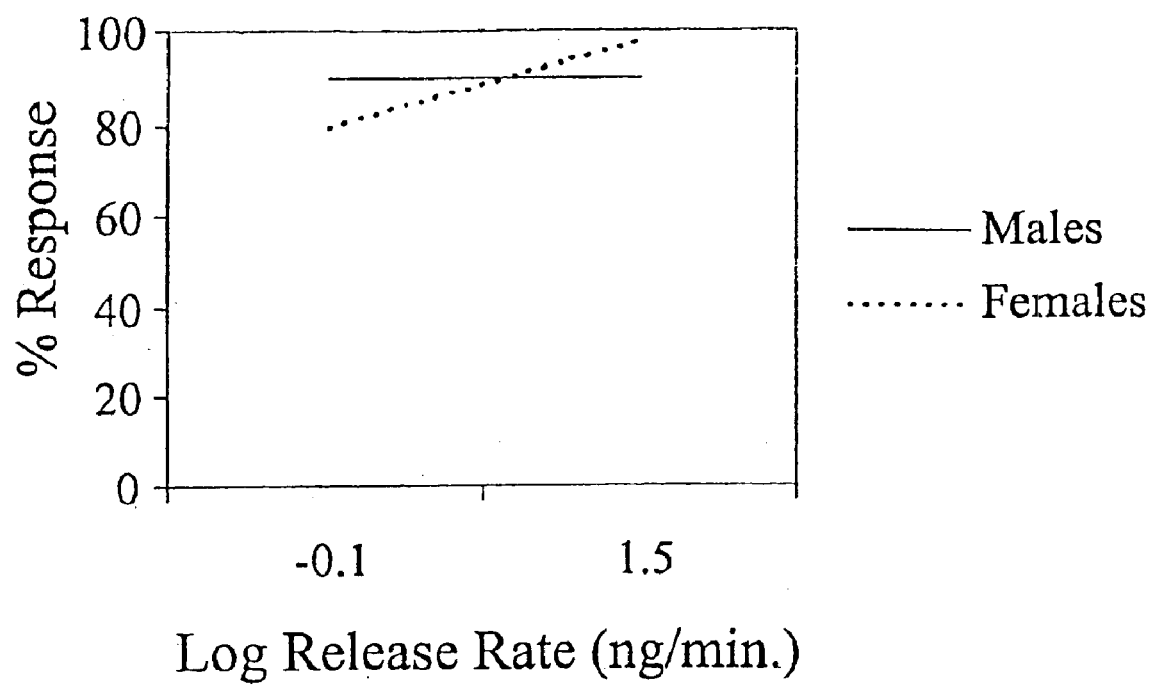
FIG. 10 is a graph showing male and female *M. croceipes* head-sticking response to about 0.08 to 33.3 ng/minute release rate of 3-Octanone. None of the control Wasps displayed the head-sticking behavior response to 3-Octanone.
Figure 11:
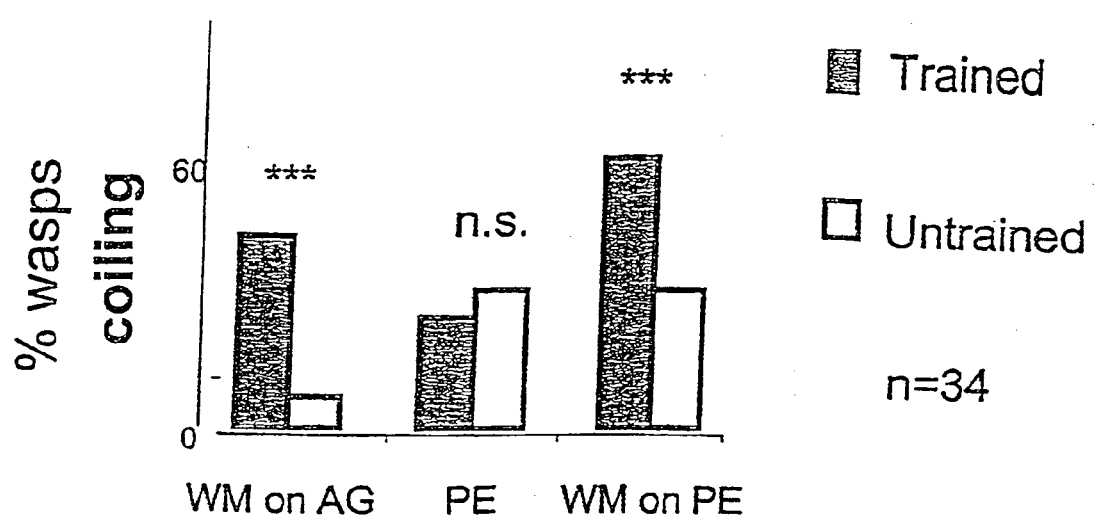
FIG. 11 is a graph showing % of trained and untrained *M. croceipes* coiling when exposed to white mold on agar, peanuts and white mold on peanuts.
Figure 12:
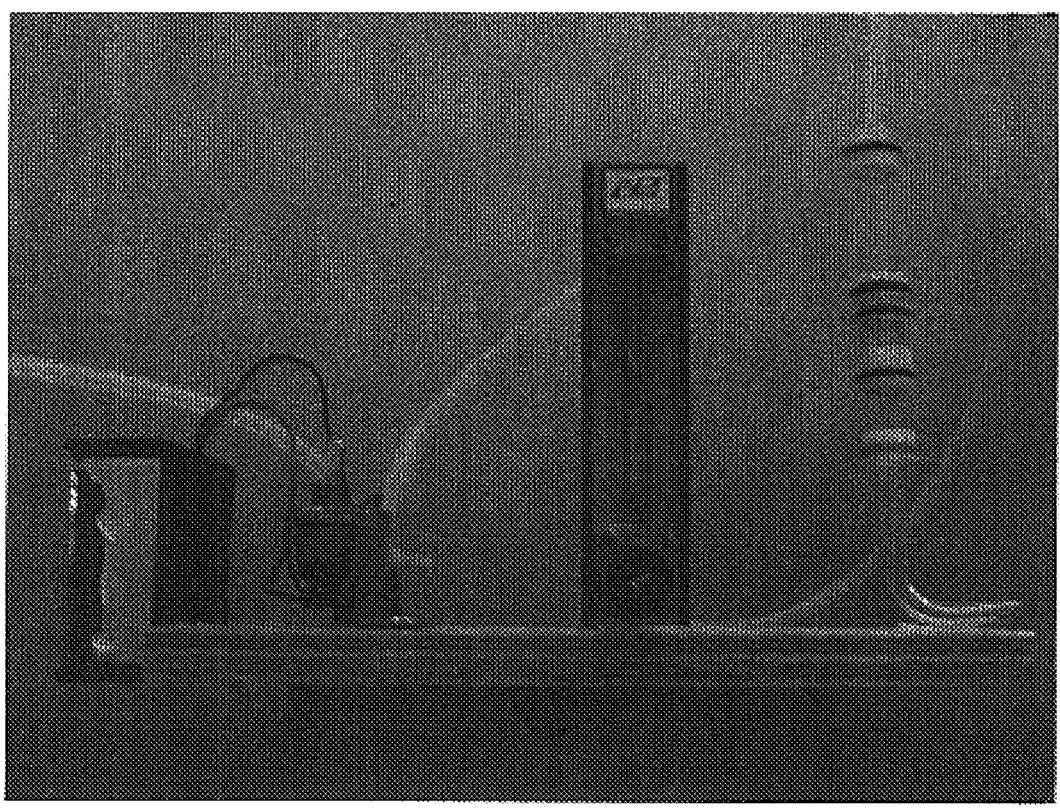
FIG. 12 is a photograph of Detector System 10.
Figure 13:
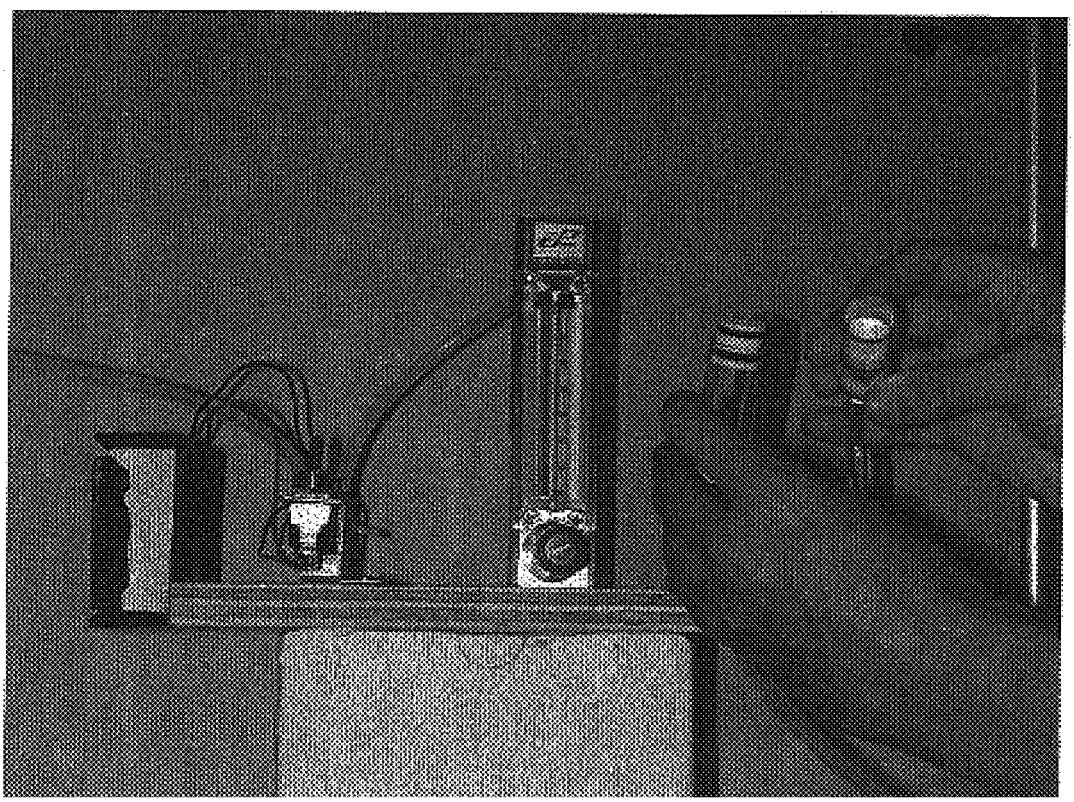
FIG. 13 is a photograph of Detector System 10 showing placement of a trained organism.
Figure 14:
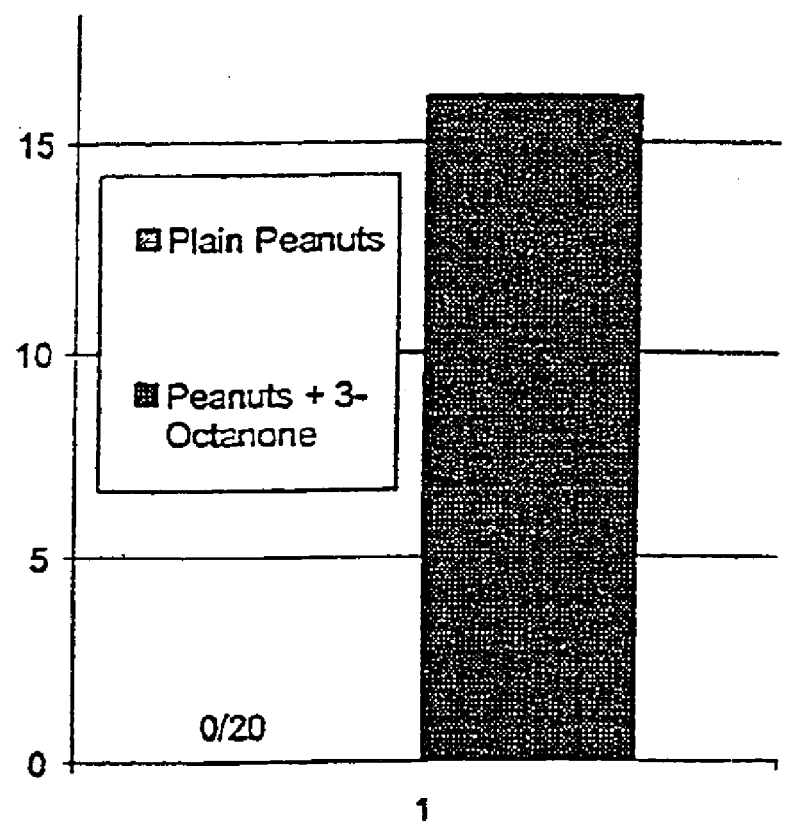
FIG. 14 is a graph showing trained female *M. croceipes* head-sticking response as a function of average time spent in the opening using Detector System 10 and 3-Octanone as the target chemical.
Figure 15:
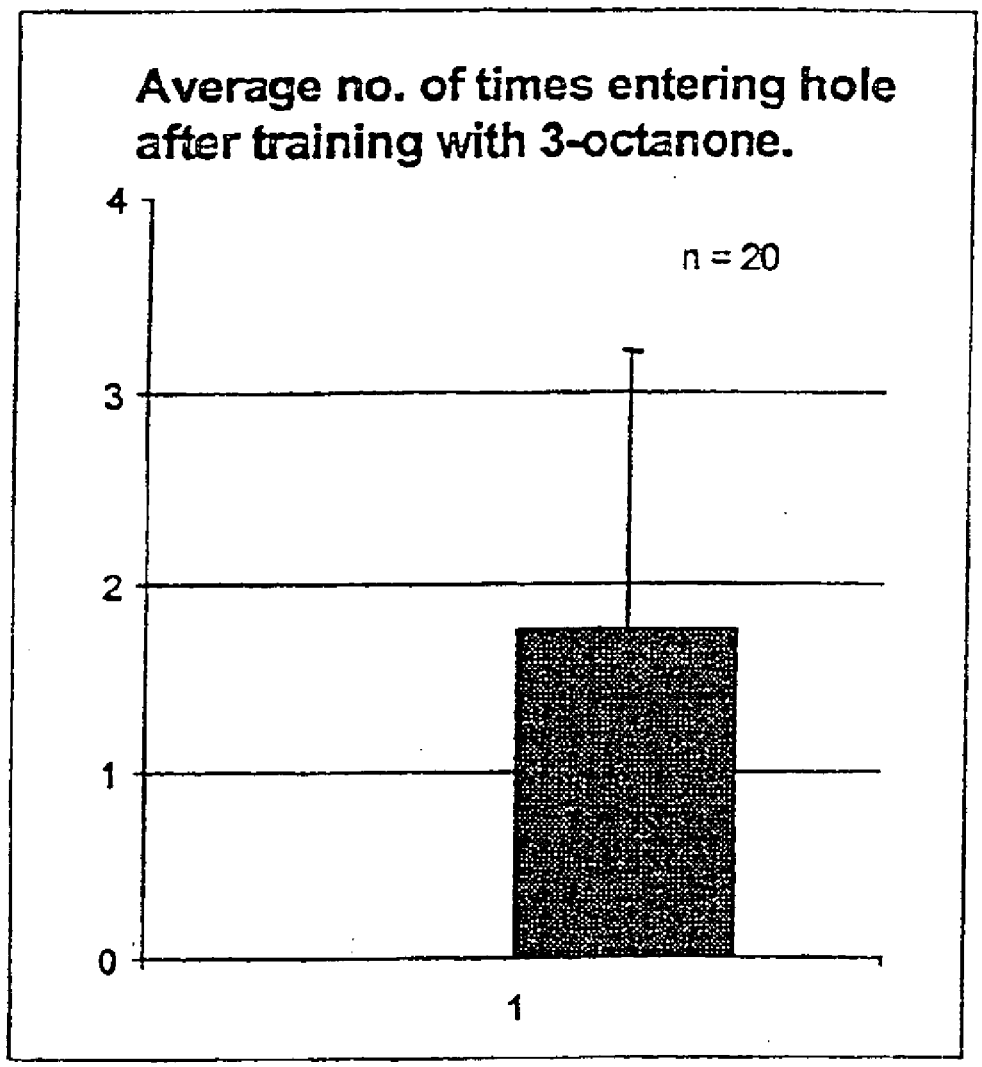
FIG. 15 is a graph showing trained female *M. croceipes* head-sticking response using Detector System 10 as a function of how many times the wasp entered the opening using 3-octanone as the target chemical.

3-octanone is the major chemical component of white mold. Wasps trained with 3-octanone odor in the presence of a food source were placed in the device of FIGS. 11 and 12. Trained wasps will exhibit head-sticking behavior (FIG. 13) when exposed to 3-octanone. Trained wasps were then placed in detection chamber 30, air was drawn into the chamber after passing over uncontaminated peanuts or peanuts with 3-Octanone applied to them and passed over the wasps. Trained wasps spent an average of 15 seconds in the opening when air was passed over peanuts with added 3-Octanone compared to no head-sticking response from the trained wasps to uncontaminated peanuts (FIG. 10). The average number of times a trained wasp entered the opening when exposed to air containing a peanut +3-Octanone was approximately 1.5+about 1.25 (FIG. 15).

Trained wasps were exposed to air from peanuts contaminated with white mold (damaged peanuts) and to damaged peanuts with added 3-Octanone (about 2 μg/hr. release rate). 2 out of 20 trained wasps displayed head-sticking behavior to the damaged peanuts and about 18 out of 20 wasps displayed head-sticking behavior when exposed to air from damaged peanuts with 3-octanone (FIG. 8). This indicates that trained wasps can detect a single learned chemical among a complex mix of other chemicals.

EXAMPLE 6

Figure 16:
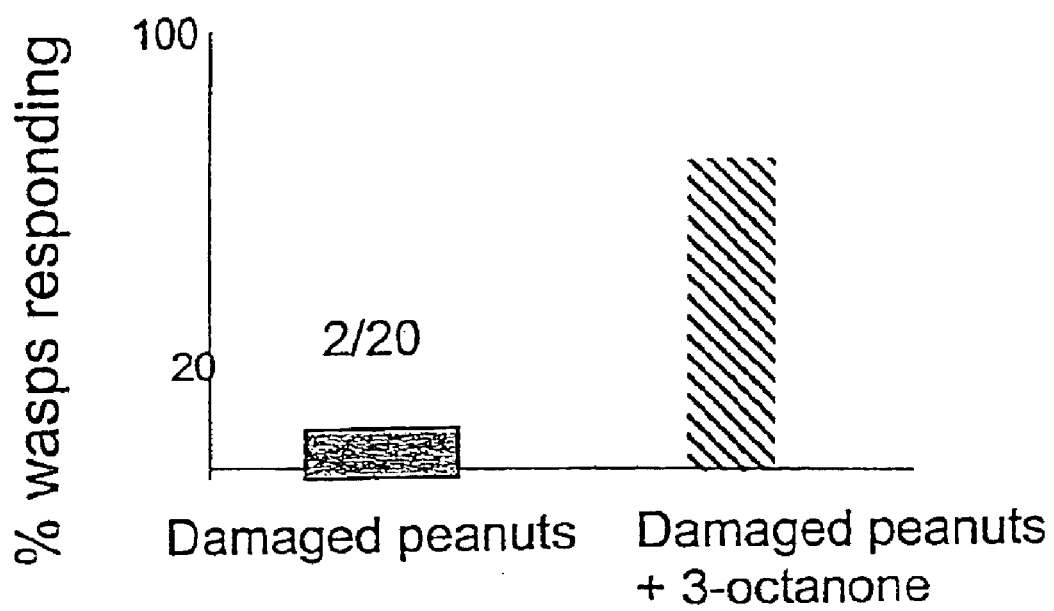
FIG. 16 is a graph showing coiling response of *M. croceipes*, after training with white mold, using damaged peanuts and damaged peanuts brushed with 3-octanone as the target chemical.
Figure 17:
FIG. 17 is a photograph showing training of *M. croceipes* using a food source while passing a target odor over the wasp.
Figure 18:
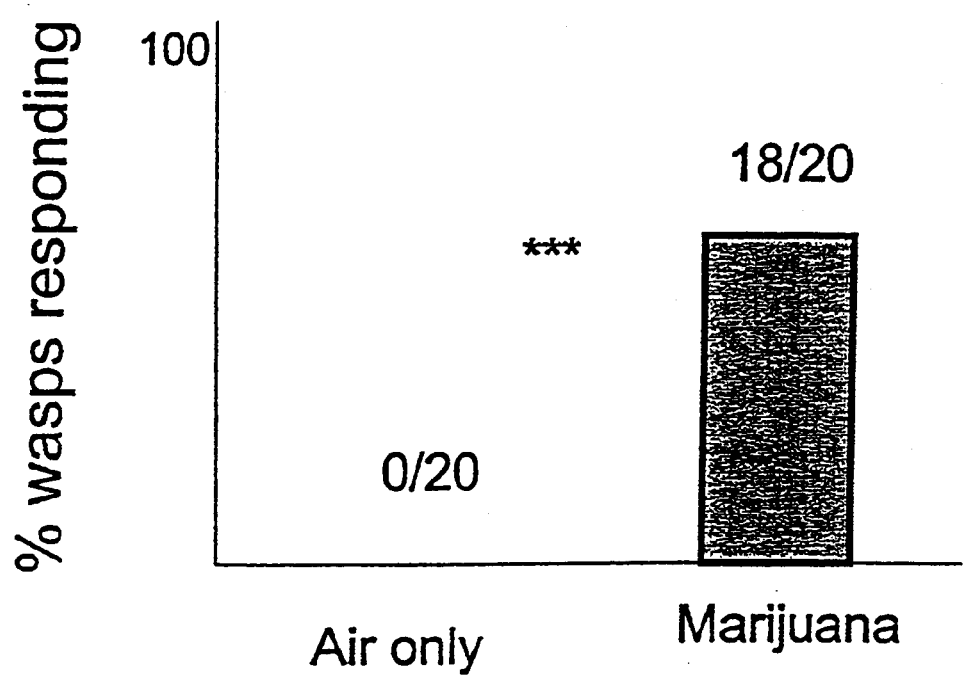
FIG. 18 is a graph showing head-sticking response after training with air only or with dried marijuana. ***$P<0.001$.

Female *M. croceipes* were placed in a detection chamber of a portable chemical detector described above and shown in FIG. 1. The wasps were trained to detect marijuana as described above in Example 4 and displayed the head-sticking behavioral response. For training, hungry wasps were presented with a sucrose solution while smelling air that was passed over dried marijuana (FIG. 15). The trained wasps were then placed in detection chamber 30, air was drawn into the chamber from a sample of dried marijuana and passed over the wasps. 18 out of 20 trained wasps exhibited the head-sticking response after training with marijuana compared to zero out of the control 20 wasps trained with air only (FIG. 16).

The above detailed description is for the purposes of illustration. Others skilled in the art can apply the knowledge described to train other invertebrates to detect chemicals for use in a system for chemical detection. Such detail is solely of theat purpose and those skilled in the art can make variations therein without departing from the spirit and scope of the invention.

Index of the Elements
10. Detector System
15. Inlet End of Valve and Meter
18. Flow Control Valve
20. Air System
21. Inlet of Air Unit
22. Air Pump
23. Outlet of Air Unit
24. Air Control Valve and Meter
25. Outlet End
26. Air Sample Inlet
27. Air Intake Unit
28. Air Sample Exhaust
29. Tubing
30. Detection Chamber
31. Outlet End of Chamber
32. Air Sample Compartment
33. Inlet End of Chamber
34. Trained Organism Compartment
35. Trained Organism
36. Divider
38. Opening
40. Power Source
50. Sensor
52. Phototransistor
54. IR LED
60. Data Analysis System
62. CR-10 Controller
64. Datalogger
66. Digital Display
68. Resistor

We claim:

1. A chemical detection system for detecting the presence of at least one chemical consisting essentially of at least one freely moving organism trained to display a recordable response behavior to at least one chemical, at least one detection chamber housing said organism, a sensor means for detecting a response by a trained organism, an air system for drawing an air sample for chemical detection into the chamber and over a freely moving trained organism, and a data analysis system operatively connected to said sensor means.

2. The system of claim 1 wherein said organism is an invertebrate.

3. The system of claim 2 wherein said invertebrate is an insect.

4. The system of claim 1 wherein said sensor is an electronic sensor.

5. The system of claim 1 wherein said system contains multiple detection chambers for determining percent response to a single chemical or for determining the presence of multiple chemicals.

6. A method for detecting the presence of at least one chemical consisting essentially of:
   (a) placing at least one organism trained to detect at least one chemical into at least one chamber wherein said one chamber includes a compartment for said organism, a sample compartment, a divider with an opening wherein said divider contains a sensor and a data analysis system for reporting said response wherein said analysis system is operatively connected to said sensor and said divider is located between said organism compartment and said sample compartment,
   (b) introducing a sample of air into said sample compartment and drawing it through said opening in said divider into the organism compartment, and
   (c) recording a response behavior of said at least one organism to determine the presence of said chemical.

7. The method of claim 6 wherein said trained organism is an invertebrate.

8. The method of claim 7 wherein said invertebrate is an insect.

9. A method for training organisms to detect at least one chemical consisting essentially of:
   (a) presenting a freely moving organism in the immediate presence of a biological resource,
   (b) drawing air from around a target chemical over said organism until it displays a response behavior to said resource,
   (c) removing said organism from said biological resource after it displays a response behavior to said resource, and
   (d) repeating steps (a)–(C) at least about two times in the immediate presence of the biological resource to obtain a trained organism which displays behavior to a target chemical without the presence of a biological resource.

10. The method of claim 9 wherein said biological resource is selected from the group consisting of food, host, mate, and prey.

11. A chemical detection system for detecting the presence of at least one chemical comprising:
   (a) a means for introducing a sample of air from an area suspected of containing a chemical into at least one detector chamber,
   (b) at least one detector chamber containing an organism trained to detect a chemical wherein said chamber is operatively connected to said means for introducing a sample of air,
   (c) a power source operatively connected to said means for introducing a sample of air,
   (d) a sensor means for detecting a response by an organism trained to detect said chemical in a sample of sir wherein said organism is in said detector chamber, and
   (e) a data analysis system operatively connected to said sensor.

12. The system of claim 11 wherein said means for introducing a sample of air into at least one detector chamber includes an air pump, a flow control valve, and a meter.

13. The system of claim 11 wherein said sensor means for detecting a response is selected from the group consisting of an infrared sensor, a visible light sensor, and a laser sensor.

14. A method for detecting the presence of at least one chemical comprising:
   (a) placing at least one organism trained to detect a chemical into a chamber comprising a compartment for said organism, a sample compartment, a divider containing a sensor and a data analysis system for reporting a response wherein said analysis system is operatively connected to said sensor and said divider has an opening wherein said divider is located between said organism compartment and said sample compartment,
   (b) introducing a sample of air into said sample compartment and drawing it through said opening in the divider into the organism compartment, and
   (c) recording a response behavior of said at least one organism to determine the presence of said chemical.

* * * * *